United States Patent [19]
Wicks et al.

[11] Patent Number: 5,756,682
[45] Date of Patent: May 26, 1998

[54] ASSAY FOR CARDIAC TROPONIN I

[76] Inventors: Richard W. Wicks, 167 Jackson Rd., St. Marys, Pa. 15857; Leslie O. Zartman, 875 Treasure Lake, DuBois, Pa. 15801; Annette M. Vargas, P.O. Box 64, Penfield, Pa. 15849; Stacy A. Torretti, 111 E. Main St., Sykesville, Pa. 15865

[21] Appl. No.: 342,101

[22] Filed: Nov. 18, 1994

Related U.S. Application Data

[62] Division of Ser. No. 63,168, May 17, 1993, abandoned.

[51] Int. Cl.⁶ .................................................. C07K 16/00
[52] U.S. Cl. ........................... 530/387.9; 530/389.1; 530/388.1; 530/388.15; 530/387.1; 530/413
[58] Field of Search .................... 530/389.1, 387.9, 530/388.1, 388.15, 387.1, 324, 327, 413

[56] References Cited

U.S. PATENT DOCUMENTS

| | | | |
|---|---|---|---|
| 4,912,033 | 3/1990 | Ladenson et al. | 435/7.4 |
| 5,290,678 | 3/1994 | Jackowski | 435/7.4 |

FOREIGN PATENT DOCUMENTS

| | | |
|---|---|---|
| 2200358 | 8/1988 | United Kingdom . |
| 2248688 | 4/1992 | United Kingdom . |
| WO 94/15217 | 7/1994 | WIPO . |

OTHER PUBLICATIONS

Larue, Catherine et al. (1993) "Cardiac–Specific Immunoenzymometric Assay of Troponin I in the Early Phase of Acute Myocardial Infarction" *Clin. Chem* 39(6):972–979.

Armour, K. et al. (1993) "Cloning and Expression in *Escherichia Coli* of the cDNA encoding Human Cardiac Troponin I" *GENE* 131:287–292.

Bodor et al. (1992) "Development of Monoclonal Antibodies for an Assay of Cardiac Troponin–I and Preliminary Results in Suspected Cases of Myocardial Infarction" *Clin. Chem.* 38(11):2203–2214.

Cummins, B. and P Cummins (1987) "Cardiac Specific Troponin–I Release in Canine Experimental Myocardial Infraction: Development of a Sensitive Enzyme–Linked Immunoassay" *J. Mol. Cell Cardiol.* 19(10):999–1010.

Cummins, B. and P. Cummins (1987) "Immunoassay of the Cardiac–Specific Isoform of Tropinin–I in the Diagnosis of Heart Muscle Damage" *Biochemical Society Transactions* 15(6):1060–1061.

Cummins et al. (1987) "Cardiac–Specific Tropinin–I Radioimmunoassay in the Diagnosis of Acute Myocardial Infarction" *Amer. Heart J.* 113(6):1333–1344.

Larue, C. et al. (1992) "New Monoclonal Antibodies as Probes for Human Cardiac Troponin I: Epitopic Analysis with Synthetic Peptides" *Molecular Immunology* 29(2):271–278.

Potter (1982) "Preparation of Troponin and Its Subnits" *Methods in Enzymology* 85:241–263.

Syska et al. (1994) "A New Method of Preparation of Troponin I (Inhibitory Protein) Using Affinity Chromatography . Evidence for Three Different Forms of Troponin in Striated Muscle" *FEBS Letters* 40(2):253–257.

Vallins, W. J. et al (1990) Molecular Cloning of Human Cardiac Troponin–I Using Polymerase Chain Reaction: FEBS, 270(1.2):57–61.

Wilkinson, J. M. and R. J. A. Grand (1978) "Comparison of Amino Acid Sequence of Troponin I From Different Striated Muscles" *Nature* 271:31–35.

*Primary Examiner*—Ponnathapura Achutamurthy
*Assistant Examiner*—T. D. Wessendorf

[57] ABSTRACT

A method for detection of cardiac troponin I is described. The method is a sandwich assay employing an antibody specific for cardiac troponin I as one binding partner and troponin C as the other binding partner for cardiac troponin I.

4 Claims, No Drawings

ASSAY FOR CARDIAC TROPONIN I

This application is a divisional of application Ser. No. 08/063,168 filed on May 17, 1993, now abandoned.

BACKGROUND OF THE INVENTION

The determination of creatine kinase MB isoenzyme (EC 2.7.3.2) in serum is currently the most widely utilized in vitro test for confirming the diagnosis of myocardial infarction ("heart attack"). While this test generally provides satisfactory results, there are some disadvantages which limit the utility of this test. One disadvantage is the relatively short period (24–48 hours) the test remains positive following an infarction. In patients who arrive at the hospital more than 48 hours after the infarct, the CK-MB test will generally not be useful in confirming the diagnosis of a heart attack. In addition to this, skeletal muscle tissue also contains small amounts of the CK-MB isoenzyme and therefore patients who suffer trauma to skeletal muscle tissue (e.g. in automobile accidents) will sometimes give false positive results and make the diagnosis of myocardial infarction more difficult.

In order to circumvent these problems, various investigators have explored alternative serum markers for myocardial damage such as the muscle protein troponin I. Troponin I is one of three subunits of the troponin complex located on the thin filament of the muscle contractile apparatus. This troponin complex plays a central role in controlling the process of muscle contraction, and therefore these three subunits are called regulatory proteins. The other two subunits (designated T and C) are also immobilized on the thin myofilaments along with troponin I in both cardiac and skeletal muscle tissue. Troponin I is encoded by different genes in cardiac, slow skeletal, and fast skeletal muscle tissues. Approximately 60% of the amino acid sequence in humans is homologous between these three forms of troponin I. The dissimiliar regions of the cardiac form make it possible to develop antibodies which will not cross react with the two skeletal forms, thus making a truly cardiac specific test possible.

Cummins, et al (1987) *American Heart Journal* 113:1333–1344 described the development of a radioimmunoassay for the measurement of cardiac troponin I in human serum. This assay utilized polyclonal antibodies having significant cross reactivity with the skeletal forms of troponin I, which limited its value in confirming the diagnosis of myocardial infarction. In addition, the test was not sufficiently sensitive to detect low levels of troponin I in serum.

Bodar, et al. (1992) *Clinical Chemistry* 38:2203–2214 described the development of a dual monoclonal antibody "sandwich" assay for troponin I in serum. While this assay showed improved cardiac specificity due to the use of mouse monoclonal antibodies, it required the use of two different monoclonal antibodies. In addition, the imprecision of the assay was unacceptably high (11–21% coefficients of variation) for a laboratory test.

SUMMARY OF THE INVENTION

The present invention relates to a process and diagnostic test system for quantitatively determining the concentration of cardiac troponin I subunit in a biological fluid. In accordance with this invention, it has surprisingly been discovered that it is possible to perform a so-called "sandwich" immunoassay, in which one immunological binding partner is a monoclonal or polyclonal antibody specific for the cardiac form of troponin I, and the other binding partner is the C subunit of the troponin complex. This process and test system provides for a rapid and specific measurement of troponin I in a biological fluid and is highly suitable for confirming the diagnosis of myocardial damage.

In general, the method of this invention comprises incubating sequentially or simultaneously a sample of the biological fluid to be tested, an antibody or antibody fragment specific for cardiac troponin I and troponin C or a troponin I-binding fragment thereof, under conditions which allow the formation of a ternary complex of troponin I in the sample, the antibody and the troponin C. The complex is separated from the sample and then detecting its formation as indicative of the amount of cardiac troponin I in the biological fluid.

DETAILED DESCRIPTION OF THE INVENTION

According to the process of the present invention, the concentration of troponin I can be quantitated in biological fluids by a sandwich immunoassay utilizing a cardiac specific antibody in combination with troponin C subunit. For this invention, it is possible to use biological fluids such as whole blood, serum, plasma, lymphatic fluid, urine, sweat, bile, amniotic fluid, cerebrospinal fluid, sputum, and the like. Fluid extracts of tissues such as heart, skeletal muscle, kidney, brain, liver, and the like can also be utilized by the process of the present invention. The preferred biological fluids for this invention however are serum or plasma.

Specifically, this invention relates to an immunoassay test system wherein two binding partners are used, each of which is capable of binding to the troponin I antigen, and one binding partner is a monoclonal or polyclonal antibody (or mixtures thereof) specific for the cardiac form of troponin I; and the second binding partner is the C subunit of the troponin complex.

In a preferred embodiment of the present invention, one of the two binding partners is immobilized on a solid phase surface, and the second binding partner is labelled or tagged with a signal generating marker. It is essential according to the present invention that the monoclonal or polyclonal antibody (or mixtures thereof) be specific for the cardiac form of troponin I, having no significant reaction with the skeletal forms of troponin I. This is due to the fact that the C subunit of troponin has substantial reactivity towards both cardiac and skeletal forms of troponin I. Using antibodies which show significant reactivity with the skeletal form of troponin I would therefore cause false positive reactions in patients with damage to skeletal tissue.

In one preferred embodiment of the present invention, monoclonal or polyclonal antibodies (or mixtures thereof) are immobilized on a suitable solid phase surface by various methods known to those in the art. The solid phase surface of the present invention is not limited to any one particular form. The solid surface can be selected from a variety of those known in the art including plastic tubes, beads, microtiter plates, latex particles, magnetic particles, cellulose beads, agarose beads, paper, dipsticks, and the like. The methods for immobilizing the antibodies or troponin C are not narrowly critical, and could include passive absorption, covalent linkage, physical trapping, and the like.

The binding partner utilized as the solid phase in the present invention can be directly affixed to the solid phase surface, or can be immobilized during the immunoassay incubation (in situ) by means known to those in the art. For example, the solid phase surface can be coated with avidin or streptavidin and the first binding partner labelled with biotin. The first binding partner can then be added in liquid phase to the biological fluid containing troponin I and labelled second binding partner. Alternatively, antibodies to goat or mouse IgG can be immobilized on the solid phase surface, and the goat or mouse monoclonal antibodies can then be added to the incubation vessel in liquid phase.

Likewise, in this one preferred embodiment of the present invention, the second binding partner (troponin C subunit) can be labelled or tagged with a variety of signal generating markers. These could include (but are not limited to) radio-isotopic labels, enzymes, chemiluminescent compounds, fluorescent labels, dyes, enzyme cofactors, biotin, and the like. The chemical linkage of the second binding partner to a signal generating marker can be accomplished by a variety of methods known to those in the art.

In a second preferred embodiment of the present invention, the troponin C subunit is immobilized on the solid phase surface and monoclonal or polyclonal antibodies (or mixtures thereof) are labelled or tagged with the signal generating marker.

The sequence of contacting the solid phase first binding partner and the labelled or tagged second binding partner with the specimen containing troponin I is not narrowly critical. In one preferred embodiment, the biological fluid containing troponin I is contacted simultaneously with solid phase first binding partner and the labelled or tagged second binding partner. This format is a so-called "simultaneous" assay and is well known to those in the art. After a suitable incubation period during which both binding partners react with the troponin I in the biological fluid to form a sandwich, the solid phase surface is washed to remove any reagents not bound to the solid phase surface, and the signal generating marker is measured by means known to those in the art.

In another embodiment of the present invention, the biological fluid containing troponin I is first contacted with the solid phase first binding partner. After a suitable incubation period during which the troponin I in the biological fluid binds to the solid phase first binding partner, the solid phase surface is washed to remove any excess troponin I and other proteins. The solid phase first binding partner is then contacted with the tagged or labelled second binding partner to complete the ternary complex or "sandwich", and a second incubation period follows during which labelled or tagged second binding partner binds to troponin I which has already been bound by solid phase first binding partner. After this second incubation period, the solid phase surface is washed to remove any excess unbound labelled second binding partner, and the signal generating marker is measured. This is a so-called "forward" type sandwich immunoassay.

Another embodiment of the present invention is a so-called "reverse" type immunoassay where the liquid phase labelled binding partner is incubated first with biological fluid containing troponin I antigen, then contacted with solid phase binding partner. After this second incubation, the solid phase is washed to remove any excess unbound reagents or proteins, and the signal generating marker is measured.

In another embodiment of the invention, a second antibody can be used to detect formation of the "sandwich". For example, a labelled antibody specific for troponin C may be used to detect the complex.

In accordance with this invention, one of the two binding partners is monoclonal or polyclonal antibodies specific for cardiac troponin I. These polyclonal antibodies can be generated in the conventional manner by injecting purified cardiac troponin I into an animal and bleeding the animal to obtain serum containing the antibody. Any of the usual means for purifying cardiac troponin I known in the art can be used to obtain the antibodies used in this invention. The polyclonal antibodies can be generated in any animal species including goats, rabbits, sheep, donkey, horse, swine, cattle, dog, monkey, and the like. In one preferred aspect of the invention the antibodies are produced in goats.

In accordance with this invention, the antibody or antibodies used as one of the binding partners must be substantially specific for the cardiac form of troponin I and have little or no reactivity with skeletal forms of troponin I.

In one preferred method of producing cardiac specific antibodies from goats, it has also been surprisingly discovered that polyclonal antibodies can be generated which show extremely low cross-reactivity with the skeletal forms of troponin I. Purified troponin I is injected into goats and the serum is collected from the animals by conventional means. A synthetic peptide corresponding to a region in the cardiac troponin I molecule which is substantially different from the skeletal troponin I molecules is synthesized by methods known to those in the art. The peptide is at least 5 amino acids, preferably at least 7 amino acids. The peptide should be at least 75%, preferably at least 90% homologous to such a region of cardiac troponin I. The peptide should differ in sequence from the corresponding region of skeletal troponin I in at least 50% of its amino acids. One such region of cardiac troponin I is the region having the sequence which is completely missing from the skeletal form:

MET—ALA—ASP—GLY—SER—SER—ASP—ALA—
ALA—ARG—GLU—PRO—ARG—PRO—ALA—PRO—ILE—
ARG—ARG—ARG—SER—SER—ASN—TYR—ARG—ALA—
TYR—ALA—THR—GLU—PRO—HIS—ALA—LYS—LYS—
LYS—SER (Seq. ID. No. 1)

A preferred segment of the above region is the peptide of the following sequence:

ARG-ALA-TYR-ALA-THR-GLU-PRO-HIS-ALA-LYS-LYS-LYS-SER and (Seq. ID. No.2)

Another region which is substantially different is:

ARG-GLY-GLU-LYS-GLY-ARG-ALA-LEU-SER-THR-ARG-CYS-GLN-PRO-LEU-GLU-LEU-ALA (Seq. ID. No.3)

The key criteria for selecting these peptides are the differences between the cardiac form of troponin I and the corresponding region of the skeletal forms of troponin I, and also the ability of these synthetic peptides to remove significant amounts of antibody from the goat anti-troponin I serum. This synthetic peptide is immobilized onto agarose beads by conventional means. The serum from the animal is contacted with the immobilized synthetic peptide to form a bond between antibodies specific for this particular peptide and the agarose beads. After a suitable contact period the beads are washed with buffer solutions and the purified cardiac specific troponin I antibodies are eluted from the beads by conventional means.

In a second preferred method of producing cardiac specific antibodies from goats, purified troponin I is injected into goats and the serum is collected from the animals by conventional means. Purified cardiac troponin I is chemically immobilized on agarose beads by conventional means. The serum from the animal is contacted with the immobilized troponin I to form a bond between the antibodies and the troponin I. After a suitable contact period, the beads are washed with buffer solutions and the purified antibodies are eluted from the beads by conventional means. The purified antibodies are then absorbed as follows to remove any antibodies which react with the skeletal forms of troponin I. Skeletal muscle troponin I is purified by conventional means and chemically immobilized on agarose beads. The purified antibodies are contacted with the resulting skeletal troponin I beads to remove essentially all those antibodies which cross react with the skeletal forms of troponin I.

In a third preferred embodiment of the present invention, cardiac specific mouse monoclonal antibodies to troponin I are produced by applying the well known cell fusion method of Kohler and Milstein (1976) *European Journal of Immunology* 6:511–519 to produce hybridomas secreting the desired antibodies. This method uses antibody producing cells from a host animal such as a mouse which has been injected with cardiac troponin I as one of two cell populations which are fused together to form an antibody secreting "hybridoma". The second cell population which is used usually consists of a cancer or myeloma cell line which will provide the ability to grow these hybridomas by tissue culture methods. The two populations of cells are fused by methods known to those in the art such as with polyethylene glycol, and the antibody producing cells are propagated by standard tissue culture methods. After obtaining a homogenous population of cells which is usually done by subcloning by the limited dilution technique, the antibody producing hybridomas are grown in vitro or in vivo by standard techniques.

The monoclonal antibodies produced in this manner can be utilized as non-purified material, however for optimal results the monoclonal antibodies are purified to a high degree of purity (e.g. greater than 95%) by methods known to those in the art. These methods can include salt precipitation, ion exchange chromatography, or affinity chromatography with immobilized protein A or immobilized protein G.

The cardiac specific antibodies used in the present invention (either polyclonal or mouse monoclonal) can be utilized as intact IgG molecules or as fragments of the molecule containing the antigen binding site. Such fragments can include Fab, Fab', or F(ab)'2 fragments prepared by digestion with enzymes such as papain, trypsin, or pepsin by means known to those in the art.

The troponin C subunit which is utilized as one of the two binding partners in the present invention can be obtained from various tissue sources and from various animal species. Skeletal muscle or cardiac tissue are two preferred sources for the troponin C subunit due to the relatively high concentrations of troponin C in these tissues. The tissue may be selected from any animal species, especially vertebrates, such as rabbits, goats, sheep, donkey, humans, horse, swine, cattle, dog, monkey, and the like. In one preferred embodiment of the present invention, the troponin C is isolated from rabbit skeletal muscle.

The troponin C can be isolated by conventional means reported in the literature e.g., Potter, et al. (1982) *Methods in Enzymology* 85:241–263. The isolation typically employs such well recognized techniques such as extraction, isoelectric precipitation, and ion exchange chromatography. Purification of the troponin C to a state of high purity (e.g. greater than 95%) is desired to obtain optimal results according to the present invention.

The troponin C can also be biosynthesized by conventional genetic engineering techniques either as the entire molecule or various fragments of the molecule. Alternatively the troponin C can be synthesized chemically by techniques of organic protein synthesis. Peptides corresponding to fragments of the troponin C molecule can also be utilized according to the present invention.

The incubation times and temperatures of the immunoassay of the present invention are not narrowly critical. Incubation times can range from 1 minute to 48 hours, but preferably these are carried out from 5 to 120 minutes. Likewise, the incubation temperatures can be carried out at temperatures from 4 degrees C. to 56 degrees C. Preferred incubation temperatures are from 20 to 37 degrees C.

Reagents for performing the assays of this invention can be assembled in kits. Such kits would include, in separate containers, antibody specific for cardiac troponin I and troponin C. The antibody or troponin C can be immobilized on a solid phase. The antibody or troponin C may be labeled. If an enzyme label is used, the kit could include the enzyme substrate. For assays employing a second antibody to label the complex, the kit would include a second antibody specific for either the antitroponin antibody or the troponin C. The kits can also contain appropriate standards, positive and negative controls and instructions for performing the assay.

The following examples further illustrate the present invention but are not intended to restrict the invention in scope or in spirit.

EXAMPLE 1

TROPONIN C PURIFICATION

I. PREPARATION OF MYOFIBRILLAR FRACTION

3 New Zealand type rabbits are sacrificed and the hind leg and back muscles removed. Excess fat is trimmed from the tissues which is then cut into 1 cm. pieces. The resulting tissue (approximately 1785 grams) is homogenized in 6 portions with a total of 4200 ml of 20 mM Tris buffer, pH 8.0 containing 50 mM potassium chloride, 2 mM ethylenediamine tetraacetic acid, 15 mM mercaptoethanol, 0.1% TRITON™ X-100 and 30 ug/ml phenyl methyl sulfonyl fluoride (wash buffer). The resulting homogenate is centrifuged for twenty minutes at 7000×g at 4 degrees C. and the resulting supernatant liquid is discarded. The resulting pellet is re-homogenized with 4200 ml of wash buffer and again centrifuged to obtain the pellet. A total of eight washes are performed in this manner. The final pellet is homogenized with 9000 ml of 25 mM Tris buffer pH 8.0 containing 1M sodium chloride, 0.1 mM calcium chloride, 1 mM mercaptoethanol (extraction buffer) and allowed to stir overnight at 4 degrees C. The resulting extract is centrifuged for one hour at 7000×g at 4 degrees C. to produce a supernatant liquid (myofibrillar fraction).

II. ISOELECTRIC PRECIPITATION

The myofibrillar fraction from step I is allowed to stir rapidly, and the pH of the solution is adjusted to 4.6 with 1N hydrochloric acid. After stirring for ten minutes, the resulting suspension is centrifuged for twenty minutes at 7000×g at 4 degrees C. The resulting pellet is discarded and the supernatant liquid is adjusted to pH 8.0 with 1N sodium hydroxide with rapid stirring. Solid ammonium sulfate is then added to the solution to a final concentration of 60% saturation, and allowed to stir overnight at 4 degrees C. to precipitate the troponin proteins.

III. DEAE SEPHAROSE PURIFICATION

The suspension from step II is centrifuged for twenty minutes at 7000×g at 4 degrees C. and the resulting pellet is dissolved in approximately 100 ml of 50 mM Tris buffer pH 8.0 containing 6M urea, 1 mM ethylenediamine tetraacetic acid, and 1 mM mercaptoethanol (DEAE buffer). The dissolved proteins are transferred to a dialysis bag and dialyzed to a final dilution of at least 1:1 million against the DEAE buffer. A 16×5 cm column of DEAE SEPHAROSE CL-6B (Pharmacia Biotech Inc., Piscataway, N.J.) is equilibrated with DEAE buffer. The dialyzed sample is applied to the column at a flow rate of 80 ml/hour and the column is washed with approximately 450 ml of DEAE buffer collecting 12 ml fractions. The flow rate is increased to 150 ml/hour and the troponin C is eluted with a gradient of 1 liter DEAE buffer and 1 liter DEAE buffer containing also 0.5M potassium chloride. Fractions containing troponin C are pooled and concentrated down to approximately 14 ml under nitrogen pressure using Millipore regenerated cellulose 10,000 cutoff membranes. The concentrated troponin C is transferred to a dialysis bag and dialyzed to a final dilution of $1/10^{12}$ against 10 mM potassium phosphate, 1M potassium chloride, pH 6.5 at 4 degrees C.

EXAMPLE 2

PURIFICATION OF TROPONIN I

I. TROPONIN C COUPLING TO GEL

In order to produce goat anti troponin I antibodies, cardiac troponin I was first isolated by the following method of Syska et al. (1974) *FEBS Letters* 40:253–257. Troponin C (approximately 500 mg) isolated by the procedure of Example 1 is coupled to ACTIGEL-ALD gel (Sterogene Corporation, Arcadia, Calif.) by washing 50 ml of the gel first with 10 mM potassium phosphate, 1M potassium chloride, pH 6.5 (coupling buffer). Troponin C is added to the gel and sodium cyanoborohydride is added to a final concentration of 0.1M. The resulting suspension is allowed to stir for four hours at ambient temperature and poured into a column to collect the gel. The gel is then washed with 225 ml of coupling buffer. The gel is removed from the column and is added to 150 ml of 10 mM potassium phosphate, 1M potassium chloride pH 6.5 containing 0.1M ethanolamine. Sodium cyanoborohydride is added to the suspension to a final concentration of 0.1M. The suspension is allowed to stir overnight at 4 degrees C. to block any unreacted coupling groups. The gel is then placed back in a column and washed with 150 ml of coupling buffer, and finally with 100 ml of 10 mM sodium phosphate pH 7.2 containing 0.15M sodium chloride and 0.05% sodium azide.

II. TROPONIN I PURIFICATION

One human heart obtained post-mortem is trimmed of excess fat and valves and cut into 1 cm. pieces at 4 degrees C. The resulting tissue (approximately 352 grams) is homogenized in one portion with 750 ml of 75 mM Tris buffer, pH 8.0 containing 8M urea, 15 mM mercaptoethanol and 1 mM calcium chloride (extraction buffer) at ambient temperature. The resulting homogenate is centrifuged for 30 minutes at 7000×g and the resulting supernatant liquid is filtered through cheesecloth to remove particles (heart extract). The troponin C coupled gel prepared in step I is placed in a column and washed with 250 ml of extraction buffer at ambient temperature. The gel is removed from the column and added to the filtered heart extract. The resulting suspension is allowed to stir for 80 minutes at ambient temperature and then centrifuged 20 minutes at 7000×g. The supernatant liquid is discarded and the pelleted gel is transferred to a column with extraction buffer. The column is washed at ambient temperature with a total of 700 ml of extraction buffer and the purified troponin I is then eluted from the column with 75 mM Tris buffer, pH 8.0 containing 8M urea, 15 mM mercaptoethanol, and 10 mM ethylenediamine tetraacetic acid (elution buffer). Fractions of 12 ml are collected and all fractions containing significant amounts of troponin I are pooled together. Sufficient 75 mM Tris buffer, pH 8.0 containing 10 mM ethylenediamine tetraacetic acid and 15 mM mercaptoethanol is added to the pooled troponin I to bring the concentration of urea from 8M to 6M. The resulting solution is concentrated under nitrogen pressure using MILLIPORE 10,000 cutoff regenerated cellulose membranes to a final volume of 14.2 ml. The final protein concentration is measured using the Bradford protein assay method and bovine albumin standards.

EXAMPLE 3

PREPARATION OF PURIFIED GOAT ANTI-TROPONIN I ANTIBODIES

I. PREPARATION OF GOAT ANTI-TROPONIN I ANTISERULM

The purified troponin I obtained from the procedure of Example 2 is mixed with an equal volume of complete Freunds adjuvant (a mineral oil suspension containing inactivated M-tuberculosis bacilli). The resulting mixture is homogenized to produce an aqueous/oil emulsion which constitutes the initial immunogen. Goats are immunized initially with an injection of immunogen containing 250 ug of cardiac troponin I prepared as in Example 2. The goats are injected monthly thereafter with 250 ug–500 ug of purified cardiac troponin I as immunogen prepared in the same manner except without the inactivated M-Tuberculosis bacilli (incomplete Freunds adjuvant). The goats are bled monthly approximately 7–10 days after injection to provide goat anti-troponin I serum.

II. PREPARATION OF SYNTHETIC TROPONIN I PEPTIDE AGAROSE BEADS

A synthetic peptide of the following formula is prepared according to solid phase methods of peptide synthesis known to those in the art:

ARG-ALA-TYR-ALA-THR-GLU-PRO-MS-ALA-LYS-LYS-LYS-SER-CYS

Briefly, the peptide was synthesized on an Applied Biosystems Model 431 automated peptide synthesizer employing Fmoc (9-fluorenylmethoxycarbonyl) as the alpha-amino protecting group. All amino acids and solvents were purchased from Applied Biosystems and were synthesis grade. Following synthesis, the peptide was cleaved from the resin and side chains were deblocked using a cleavage cocktail containing 6.67% phenol, 4.4% (v/v) thioanisole and 8.8% ethanedithiol in trifluoroacetic acid. The cleaved peptide was precipitated and washed several times in cold diethyl ether. It was then dissolved in water and lyophilized. The crude peptide was subjected to amino acid analysis (Waters PICO-Tag™ System) and reversed-phase HPLC using a VYDAC™ C8 column with 0.1% TFA in water and 99.9% acetonitrile in 0.1% TFA as the mobile buffers. The presence of a single major peak along with the appropriate amino acid composition was taken as evidence that the peptide was suitable for further use.

TABLE I

AMINO ACID COMPOSITION OF TROPONIN I PEPTIDE

| AMINO ACID | MOLE % (HIS = 1.0) |
|---|---|
| ASP + ASN | 0.013 |
| GLU + GLN | 0.95 |
| SER | 0.58 |
| GLY | 0.012 |
| HIS | 1.00 |
| ARG | 1.02 |
| THR | 1.00 |
| ALA | 2.98 |
| PRO | 1.02 |
| TYR | 0.98 |
| VAL | 0.008 |
| MET | 0.24 |
| CYS 2 | 0.14 |
| ILE | 0.009 |
| LEU | 0.03 |
| PHE | 0.006 |
| LYS | 3.13 |

The resulting peptide is coupled to 6% cross linked agarose beads (SULFOLINK™ gel, Pierce Chemical Company, Rockford, Ill.) by dissolving 10 mg of peptide by weight in 20 ml of 50 mM Tris pH 8.5 containing 5 mM ethylenediamine tetraacetic acid (EDTA). 10 ml of SULFOLINK™ gel is washed in a column with 120 ml of 50 mM Tris buffer pH 8.5 containing 5 mM EDTA (coupling buffer). The resulting washed gel is added to the solution of troponin I peptide and allowed to stir for 4 hours at ambient temperature and 16 hours at 4 degrees C. The resulting suspension is poured into a column and washed with 30 ml of coupling buffer. The gel is removed from the column and added to 20 ml of coupling buffer containing in addition, 50 mM mercaptoethanol to block any remaining reactive groups. This suspension is allowed to stir for 60 minutes at ambient temperature and then washed with 40 ml of 1M sodium chloride solution and 40 ml of 5 mM imidazole pH 7.2 containing 0.15M sodium chloride and 0.05% sodium azide.

III. ISOLATION OF CARDIAC SPECIFIC TROPONIN I ANTIBODIES

Antiserum prepared in step I is collected and 56 ml is diluted with 56 ml of 5 mM imidazole buffer pH 7.2 containing 0.15M sodium chloride. Phenylmethyl sulfonyl fluoride (PMSF), leupeptin, aprotinin, and pepstatin A are added to final concentrations of 15 ug/ml, 0.5 ug/ml, 0.5 ug/ml and 0.75 ug/ml respectively in order to inhibit proteases in the antiserum. The synthetic peptide gel prepared in step II is added to the diluted antiserum and allowed to stir for 1 hour at ambient temperature. The resulting mixture is transferred to a column and washed with 55 ml of 5 mM imidazole pH 7.2 containing 1M sodium chloride and 0.05% sodium azide at ambient temperature. The purified cardiac specific antibodies are eluted from the gel with 55 ml of first elution buffer (IMMUNOPURE GENTLE AG/AB Elution Buffer, Pierce Chemical Company, Rockford, Ill.) followed by 55 ml of second elution buffer (5 mM imidazole pH 7.0 containing 3M sodium thiocyanate and 0.05% sodium azide). The purified antibodies contained in both these eluates are dialyzed to a final dilution of $10^6$ against 5 mM imidazole pH 7.2 containing 0.15M sodium chloride, concentrated under nitrogen pressure to approximately 25 ml and then dialyzed to a final dilution of $10^9$ in 10 mM sodium phosphate pH 7.2 containing 0.15M sodium chloride and 0.05% sodium azide. The resulting dialyzate is then centrifuged for 15 minutes at 7000×g to remove insoluble material. The protein concentration of the resulting supernatant liquid containing purified cardiac- specific troponin I antibodies is determined spectrophotometrically at 280 mm using an extinction coefficient of E 1%=13.0.

EXAMPLE 4

PREPARATION OF TROPONIN C ALKALINE PHOSPHATASE

I. Troponin C prepared by the method of Example 1 is chemically linked to alkaline phosphatase by the following procedure. Troponin C (3 mg) in a volume of 107 ul is treated with 25 ul of SATA (N-succinimidyl S-Acetylthioacetate, Pierce Chemical Company, Rockford, Ill.) solution prepared at a concentration of 7 mg/ml in dimethyl sulfoxide. After allowing the reaction solution to stir for 30 minutes at room temperature, the solution is dialyzed overnight against 2 liters of 50 mM sodium phosphate pH 7.5 containing 2 mM EDTA at 4 degrees C. The SATA modified troponin C is deacetylated by adding hydroxylamine to a final concentration of 50 mM and allowing the solution to stand at ambient temperature for two hours. The modified troponin C is then dialyzed overnight against 2 liters of 30 mM triethanolamine pH 7.2 containing 2 mM EDTA. Six mg of alkaline phosphatase (AP) from calf intestine (Biozyme Corporation, San Diego, Calif.) in a volume of 1.55 ml is placed in a glass test tube. A fresh solution of sulfo-SMCC (sulfosuccinimidyl 4[N-maleimidomethyl]cyclohexane-1-carboxylate, Pierce Chemical Company, Rockford, Ill.) is prepared at a concentration of 5 mg/ml in deionized water. A total of 87 ul of the SMCC solution is added to the AP and allowed to stir for one hour at ambient temperature. The modified AP solution is then dialyzed overnight against 2 liters of 30 mM triethanolamine pH 7.2 containing 5 mM magnesium chloride and 1 mM zinc chloride at 4 degrees C. A total of 1.35 mg of the SATA modified troponin C is mixed with 4 mg of SMCC modified AP and allowed to stir for 24 hours at 4 degrees C. Mercaptoethylamine and iodoacetamide are added to the solution to a final concentration of 10 mM and allowed to stir for 20 minutes at ambient temperature. The resulting AP conjugated troponin C is then passed over a 1.5×90 cm column of SEPHACRYL S-300 (Pharmacia Biotech Inc., Piscataway, N.J.) to purify the AP troponin C conjugate from unreacted products.

EXAMPLE 5

PURIFICATION OF HUMAN SKELETAL TROPONIN I

I. PREPARATION OF MYOFIBRILLAR FRACTION

Human skeletal muscle tissue (pectoral muscle) is thawed at 4 degrees C. and trimmed of fatty material. A total of 83.6 grams of tissue is cut into 1 cm pieces and homogenized in 750 ml of 20 mM Tris pH 8.0 containing 50 mM potassium chloride, 2 mM EDTA, 1% Triton X-100 detergent, 15 mM mercaptoethanol, and 30 ug/ml PMSF (wash buffer 1) for 60 seconds. The resulting homogenate is centrifuged 25 minutes at 7000×g and the supernatant liquid is discarded. The resulting pellet is re-homogenized with 750 ml of wash buffer 1 and again centrifuged to obtain the pellet. A total of seven washes are performed in this manner. The pellet is then washed three times with wash buffer 2 (20 mM Tris pH 8.0 containing 50 mM potassium chloride, 2 mM EDTA, 15 mM mercaptoethanol and 30 ug/ml PMSF) in the same manner. The resulting pellet is homogenized in 750 ml of 35 mM Tris pH 7.7 containing 0.6M potassium iodide, 0.1M sodium chloride, 5 mM magnesium chloride, 1 mM EDTA, 5 mM adenosine triphosphate (ATP), 5 mM mercaptoethanol, 30 ug/ml PMSF, 1.3 ug/ml leupeptin, and 1.3 ug/ml pepstatin A. The resulting suspension is allowed to stir for 15 minutes at 4 degrees C. and then centrifuged for 30 minutes at 7000×g. The resulting supernatant liquid is dialyzed to a final dilution of 1/200 against 35 mM Tris pH 7.7 containing 50 mM sodium chloride, 1 mM magnesium chloride, 0.1 mM EDTA, 30 ug/ml PMSF, 1 mM ATP, and 2 mM mercaptoethanol. The resulting solution is centrifuged for 30 minutes at 7000×g and the supernatant liquid retained.

II. DEAE SEPHAROSE™ CHROMATOGRAPHY

Solid ammonium sulfate is added to the supernatant liquid from step I to a final concentration of 80% saturation. After allowing the suspension to stir for 2½ hours at 4 degrees C., the suspension is centrifuged for 30 minutes at 7000×g. The supernatant liquid is discarded and the pellet dissolved in 200 ml of 50 mM Tris pH 8.0 containing 9M urea, 0.5 mM EDTA, 15 mM mercaptoethanol, and 30 ug/ml PMSF. The resulting solution is dialyzed to a final dilution of $10^4$ against 50 mM Tris pH 8.0 containing 6M urea, 0.5 mM EDTA, 15 mM mercaptoethanol and 30 ug/ml PMSF at 4 degrees C. (DEAE buffer). The resultant solution is applied to a 13×4.8 cm column of DEAE—SEPHAROSE CL-6B column equilibrated with DEAE buffer at ambient temperature at a flow rate of 90 ml/hour. Fractions of 10 ml are collected and the effluent fractions containing troponin I are pooled together. The resulting pool is concentrated under nitrogen pressure with Millipore regenerated cellulose membranes to a final volume of 5 ml.

III. GEL FILTRATION CHROMATOGRAPHY

The concentrated troponin I sample from step II is applied to a 2.5×90 cm. column of SEPHAROSE S-300 gel equilibrated at 4 degrees with DEAE buffer at a flow rate of 30 ml/hour. Fractions containing purified skeletal troponin I are pooled together and dialyzed to a final dilution of 1/100 in 10 mM Tris pH 8.0 containing 1 mM EDTA and 6M urea. The final protein concentration is determined by the method of Bradford using bovine albumin standards.

EXAMPLE 6

IMMUNOCHEMICAL ASSAY FOR TROPONIN I

I. SIMULTANEOUS SANDWICH TROPONIN I IMMUNOASSAY

Purified troponin I antibodies prepared according to Example 3 are diluted to 10 ug/ml in 100 mM sodium citrate pH 4.0 containing 0.05% sodium azide. The antibodies are coated overnight at ambient temperature in a volume of 100 ul to polystyrene microtiter plates (Dynatech Corp., Chantilly, Va.). The microtiter plates are washed three times with 10 mM Tris buffer pH 7.2 containing 1M sodium chloride and blocked with a solution containing 10 mM Tris pH 7.2, 10% gluconic acid, 1% bovine serum albumin and 0.05% Proclin-300™ (Rohm and Haas, Philadelphia, Pa.) for one hour at ambient temperature. Excess liquid is aspirated from the microtiter plate wells and the plates are allowed to dry at ambient temperature. The antibody coated plates are then stored at 4 degrees until use. Purified cardiac troponin I prepared as in Example 2 is diluted in troponin I—free normal human serum to final concentrations of 5, 25 and 50 ng/ml to provide standards for the immunoassay. Troponin C labelled alkaline phosphatase prepared as in Example 4 is diluted to 5 ug/ml concentration in 50 mM triethanolamine pH 7.4 containing 20% heat inactivated goat serum, 1 mM magnesium chloride, 0.1 mM zinc chloride and 0.05% sodium azide.

Serum samples or troponin I standards (20 ul) are added in duplicate to the antibody coated microtiter plate wells prepared previously. Troponin C labelled AP (80 ul) is then added to the wells and incubated two hours at ambient temperature. The microtiter plate wells are then washed five times with deionized water and a substrate solution (100 ul) of 0.83 mg/ml paranitrophenyl phosphate in 25 mM diethanolamine pH 9.80 containing 5 mM magnesium chloride, 0.1 mM zinc chloride, 0.02% TWEEN™ 20, and 0.05% PROCLIN-300™ is then added to all the wells. The substrate solution is allowed to incubate 30 minutes at ambient temperature and the reaction is stopped by the addition of 100 ul of 2N sodium hydroxide. Absorbance of the solutions in the microtiter plates are then read at 405 nm with a suitable reader. A typical standard curve is shown in table II.

TABLE II

| TROPONIN I CONCENTRATION | |
|---|---|
| (ng/ml) | MEAN $A^{405\ nm}$ |
| 0 | 0.075 |
| 5 | 0.105 |
| 25 | 0.194 |
| 50 | 0.359 |

EXAMPLE 7

CHARACTERIZATION OF TROPONIN I IMMUNOASSAY

I. Serum collected from patients who had a documented myocardial infarction (MI serum) and serum from normal healthy subjects (Normal serum) were tested in the troponin I immunoassay according to Example 6. In addition, skeletal troponin I, prepared as in Example 5, was added to normal serum at a final concentration of 29 ug/ml to determine cross reactivity of the assay with skeletal troponin I.

As seen in table III, the assay of the present invention clearly differentiates those patients suffering from a heart attack from normal subjects. In addition, the assay system shows<0.01% reactivity with the skeletal form of troponin I.

TABLE III

| | TROPONIN I |
|---|---|
| SAMPLE | CONCENTRATION (ng/ml) |
| MI SERUM #1 | >50 ng/ml |
| MI SERUM #2 | 15.5 ng/ml |
| MI SERUM #3 | >50 ng/ml |
| NORMAL SERUM #1 | 0 ng/ml |
| NORMAL SERUM #2 | 0 ng/ml |
| NORMAL SERUM #3 | 0 ng/ml |
| NORMAL SERUM #4 | 0 ng/ml |
| NORMAL SERUM #5 | 0 ng/ml |
| NORMAL SERUM (+29,000 ng/ml skeletal troponin I) | 6 ng/ml |

EQUIVALENTS

Those skilled in the art will recognize, or be able to ascertain, by no more than routine experimentation, many equivalents of the specific embodiments of the invention described herein. Such equivalents are intended to be encompassed by the following claims.

We claim:

1. Polyclonal antibodies which bind specifically to the peptide

ARG-GLY-GLU-LYS-GLY-ARG-ALA-LEU-SER-THR-ARG-CYS-GLN-PRO-LEU-GLU-LEU-ALA (SEQ ID NO: 3):

said polyclonal antibodies having essentially no cross-reactivity with skeletal troponin I.

2. Monoclonal antibody specific for the peptide:

ARG-GLY-GLU-LYS-GLY-ARG-ALA-LEU-SER-THR-ARG-CYS-GLN-PRO-LEU-GLU-LEU-ALA (SEQ ID NO: 3).

3. A method for preparing polyclonal antibodies specific for cardiac troponin I comprising:

(i) contacting anti-troponin I antiserum with the peptide ARG-GLY-GLU-LYS-GLY-ARG-ALA-LEU-SER-THR-ARG-CYS-GLN-PRO-LEU-GLU-LEU-ALA (SEQ ID NO: 3), under conditions which permit antibodies specific for the peptide to bind to the solid phase;

(ii) separating the solid phase from the antiserum; and (iii) thereafter eluting the bound antibodies from the solid phase.

4. The method of claim 3, wherein the anti-troponin I antiserum is prepared by immunizing an animal with purified cardiac troponin I.

* * * * *

UNITED STATES PATENT AND TRADEMARK OFFICE
CERTIFICATE OF CORRECTION

PATENT NO. : 5,756,682
DATED : May 26, 1998
INVENTOR(S) : Richard W. Wicks et al.

It is certified that error appears in the above-identified patent and that said Letters Patent is hereby corrected as shown below:

On the title page, under item [56].

Attorney, Agent, or Firm - Lahive & Cockfield, LLP

Signed and Sealed this

Eleventh Day of May, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

```
Met Ala Asp Gly Ser Ser Asp Ala Ala Arg Glu Pro Arg Pro Ala Pro
 1               5                  10                  15
Ala Pro Ile Arg Arg Arg Ser Ser Asn Tyr Arg Ala Tyr Ala Thr Glu
            20                  25                  30
Pro His Ala Lys Lys Lys Ser
            35
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
Arg Ala Tyr Ala Thr Glu Pro His Ala Lys Lys Lys Ser
 1               5                  10
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

```
Arg Gly Glu Lys Gly Arg Ala Leu Ser Thr Arg Cys Gln Pro Leu Glu
 1               5                  10                  15
Leu Ala
```